United States Patent [19]
Woodward

[11] Patent Number: 5,145,370
[45] Date of Patent: Sep. 8, 1992

[54] DENTAL FIBEROPTIC HANDPIECE HOSE ASSEMBLY

[76] Inventor: Gary Woodward, 9301 S.W. Sagert, Apt. 29 Tualatin, OR 97062

[21] Appl. No.: 576,266
[22] Filed: Aug. 31, 1990

Related U.S. Application Data

[63] Continuation-in-part of Ser. No. 317,833, Mar. 1, 1989, Pat. No. 4,975,058.

[51] Int. Cl.⁵ .............................................. A61C 1/08
[52] U.S. Cl. ..................................................... 433/126
[58] Field of Search ................... 433/126, 29; 403/289, 403/290, 309, 310, 313, 314

[56] References Cited

U.S. PATENT DOCUMENTS

| | | | |
|---|---|---|---|
| 50,190 | 9/1865 | Watson | 403/310 |
| 1,904,061 | 4/1933 | Larson | 403/290 X |
| 2,345,750 | 4/1944 | Hohwart | 403/314 X |
| 2,618,496 | 11/1952 | Johnson | 403/290 |
| 2,701,147 | 2/1955 | Summerville | 433/126 X |
| 2,797,943 | 7/1957 | Carpenter | 403/313 X |
| 2,932,294 | 4/1960 | Fourestier et al. | 433/29 X |
| 3,010,357 | 11/1961 | Hirschowitz | 433/29 X |
| 3,521,359 | 7/1970 | Harris | 433/126 |
| 3,893,242 | 7/1975 | Lieb et al. | 433/29 |
| 4,014,098 | 3/1977 | Scrivo et al. | 433/126 X |
| 4,080,737 | 3/1978 | Fleer | 32/22 |
| 4,141,619 | 2/1979 | DeLuca | 403/290 X |
| 4,175,323 | 11/1979 | Eibofner et al. | 433/126 |
| 4,182,038 | 1/1980 | Fleer | 433/85 |
| 4,260,382 | 4/1981 | Thomson | 433/126 |
| 4,303,392 | 12/1981 | Rollofson | 433/126 |
| 4,341,518 | 7/1982 | wallace | 433/29 |
| 4,353,697 | 10/1982 | Nakanishi | 433/126 |
| 4,375,964 | 3/1983 | Knopp et al. | 433/29 |
| 4,388,012 | 6/1983 | Erickson | 403/313 X |
| 4,403,957 | 9/1983 | Mossle et al. | 433/29 |
| 4,403,959 | 9/1983 | Hatakeyama | 433/126 |
| 4,477,253 | 10/1984 | Euvard | 433/126 |
| 4,507,085 | 3/1985 | Mosimann | 433/126 |
| 4,521,189 | 1/1985 | Lares et al. | 433/84 |
| 4,541,802 | 9/1985 | Olsen | 433/126 |
| 4,553,938 | 11/1985 | Olsen | 433/126 |
| 4,579,879 | 4/1986 | Flynn | 523/112 |
| 4,614,498 | 9/1986 | Vaccaro | 433/29 X |
| 4,626,210 | 12/1986 | Malata et al. | 433/29 |
| 4,710,052 | 12/1987 | Elger | 403/310 |
| 4,765,199 | 8/1988 | Andersen et al. | 403/290 X |
| 4,802,752 | 2/1989 | Anglin | 403/314 X |
| 4,902,045 | 2/1990 | McGugan | 403/289 X |
| 4,925,668 | 5/1990 | Khan et al. | 424/422 |
| 4,978,297 | 12/1990 | Vlock | 433/126 X |
| 5,004,367 | 4/1991 | Wood, Jr. | 403/314 X |
| 5,035,528 | 7/1991 | Thau | 403/290 |

FOREIGN PATENT DOCUMENTS

| 0017318 | 10/1980 | European Pat. Off. | 17/96 |
|---|---|---|---|
| 2618158 | 3/1977 | Fed. Rep. of Germany | 433/126 |
| 2908390 | 9/1979 | Fed. Rep. of Germany | 433/126 |
| 3716410 | 11/1987 | Fed. Rep. of Germany | 433/29 |
| 2250361 | 5/1975 | France | 403/309 |
| 1349227 | 4/1974 | United Kingdom . | |

*Primary Examiner*—Gene Mancene
*Assistant Examiner*—Nicolas D. Lucchesi
*Attorney, Agent, or Firm*—Quirk, Tratos & Roethel

[57] ABSTRACT

A dental fiberoptic handpiece hose assembly comprises a flexible aspetic outer tubing that contains internally a plurality of conduits and wires for the drive air, exhaust air, coolant water and "chip" air, as well as a fiberoptic bundle and a sensing cable. The outer surface of the tubing is quite smooth and regular without any crevices that would trap bacteria. The outer surface tubing is made from an oil resistant material to discourage cracking and to improve the useful life of the hose assembly. The fiberoptic bundle comprises an acrylic material that is lightweight and flexible. The connection between the handpiece and the hose assembly is a swivelable construction that is quite simple to fabricate. A specially designed adapter is mounted inside the swivel connection and is utilized to connect the conduits of the drive air, exhaust air, chip and and coolant water as well as the fiberoptic bundle and the sensing cable to the handpiece. The fiberoptic bundle connects in an easily releasable manner to the adapter and the sensing cable is also securely attached to the adapter. This construction of the adapter allows access to the interior conduits and the fiberoptic bundle to allow repairability of the hose assembly in the field. In an alternate embodiment, a double swivel is provided to increase the swivelability of the handpiece. A quick disconnect construction is used to allow rapid and simple removal of the handpiece from the hose assembly.

57 Claims, 7 Drawing Sheets

DENTAL FIBEROPTIC HANDPIECE HOSE ASSEMBLY

CROSS-REFERENCE TO RELATED APPLICATION

This application is a Continuation-in-Part Application of application Ser. No. 07/317,833, filed Mar. 1, 1989, now U.S. Pat. No. 4,975,058.

BACKGROUND OF THE INVENTION

This application relates to dental fiberoptic handpiece hose assemblies, and more particularly to dental fiberoptic handpiece hose assemblies that are field-serviceable, that also contain a swivel connection member and that are connected to the handpiece by a quick disconnect construction.

In the modern dental office, one of the main pieces of equipment used by the dentist is the handpiece. The handpiece is connected to its power supply by a long, flexible hose. The hose contains parallel passageways for transmitting drive air, chip air, water and light to the handpiece and for removing exhaust air from the handpiece.

A typical commercially available hose has four passageways for the air and liquid transmissions and a fifth central passageway containing a fiberoptic bundle for transmitting light to an illuminator located in the handpiece to provide extra light to assist the dentist during the cutting, polishing or other activities in the patient's oral cavity. Another conventional hose comprises a flexible outer tube, often cloth-covered, that contains a plurality of separate conduits or tubings for transmitting the air, water and light to the handpiece.

Representative of these conventional assemblies is that shown in U.S. Pat. No. 4,553,938 (Olsen).

During dental operations the handpiece is often twisted, rotated or reoriented to allow the dentist to work at all angles in the patient's oral cavity. In order to permit this twisting, rotating and reorientation, the hose needs to be attached to the handpiece by a swivel arrangement. Various assemblies have been proposed to allow for a maximum amount of swiveling, such as the assembly shown in the above-referenced Olsen patent. Also representative of swivelable handpieces assembly are U.S. Pat. No. 4,303,392 (Rollofson) and U.S. Pat. No. 4,080,737 (Fleer).

Also during use of the dental handpiece, it is a common occurrence that leaks or blockages will occur in the fluid lines that transmit the air and water to the handpiece. It would be preferable if the fiberoptic handpiece and hose could be serviced in the field—that is, in the dentist's office—without the necessity of simply replacing the entire assembly or returning the assembly to the repair shop, neither of which is cost effective. Because returning the parts to the repair shop is not cost effective, the current practice is to simply replace the entire hose assembly rather than repairing it at all.

The conventional fiberoptic bundle is made of glass fibers and is also a problem area in that it is relatively quite heavy and non-flexible. The weight of the fiberoptic bundle increases the fatigue encountered by the dentist during his workday. The non-flexibility of the fiberoptic bundle increases the likelihood of breaks occurring in the fiberoptic line during the twisting rotating and reorientation of the hose that occurs during the use of the handpiece.

Many conventional fiberoptic handpieces are also touch-activated—that is, the fiberoptic bundle is activated by the touch of the operator to transmit light to the handpiece. This is accomplished by the use of a metal adapter mounted in the connection between the hose and the handpiece. The fiberoptic bundle is attached to the metal adapter and the adapter detects the touch of the operator to activate the fiberoptic bundle which causes light to be transmitted to the handpiece. The use of metal, however, in the adapter adds to the overall weight of the assembly.

It is an object of the present invention that the dental handpiece can be connected to the hose by a swivel member assembly that is field-serviceable.

It is a feature of the present invention that the connection between the hose assembly and the dental handpiece is releasable to allow access to the internal components to permit servicing in the field. The hose is attached to the rear end of the swivel member assembly to allow easy access to the internal components of the assembly.

It is an advantage of the present invention that leaks or blockages in the air or liquid transmitting components or breakages in the fiberoptic bundle can be repaired in the field without the necessity of replacing the entire assembly or returning the entire assembly to the repair shop.

It is a further object of the present invention to provide a swivel connection member assembly whose construction permits the interior of the handpiece to be field-serviceable.

It is a further object of the present invention to provide a variety of different types of swivel connection members to accommodate the different structures presently on the market, including a double swivel arrangement for improved utility of the hose assembly and its associated handpiece while still maintaining field-serviceability.

It is a further object of the present invention to provide an improved fiberoptic bundle that is more flexible and lightweight than the presently used fiberoptic bundles. The fiberoptic bundle is also oil resistant and covered with a translucent sheathing.

It is a further object of the present invention to provide an improved touch-activated adapter that activates the fiberoptic bundle to provide light to the dentist's working area.

It is a further object of the present invention to provide a handpiece hose assembly made of lightweight materials to reduce the overall weight of the hose assembly and therefore decrease the fatigue of the dentist.

It is a further object of the present invention to provide a quick disconnect construction between the handpiece hose assembly and the handpiece to permit quick replacement of the handpiece on the hose assembly.

It is a further object of the present invention to provide an aseptic outer tubing with increased oil resistance to improve and lengthen the useful life of the hose assembly.

SUMMARY OF THE INVENTION

A dental fiberoptic handpiece hose assembly comprises a flexible aseptic outer tubing that contains internally a plurality of conduits and wires for the drive air, exhaust air, coolant water and "chip" air, as well as a fiberoptic bundle and a sensing cable. The outer surface of the tubing is quite smooth and regular without any crevices that would trap bacteria. The outer surface tubing is made from an oil resistant material to discourage cracking and to improve the useful life of the hose assembly. The fiberoptic bundle comprises an acrylic material that is lightweight and flexible. The connection between the handpiece and the hose assembly is a swivelable construction that is quite simple to fabricate.

A specially designed adapter is mounted inside the swivel connection and is utilized to connect the conduits of the drive air, exhaust air, chip air and coolant water as well as the fiberoptic bundle and the sensing cable to the handpiece. The fiberoptic bundle connects in an easily releasable manner to the adapter and the sensing cable is also securely attached to the adapter. This construction of the adapter allows access to the interior conduits and the fiberoptic bundle to allow repairability of those components of the hose assembly in the field.

In an alternate embodiment, a double swivel is provided to increase the swivelability of the handpiece. A quick disconnect construction is used to allow rapid and simple removal of the handpiece from the hose assembly.

DETAILED DESCRIPTION OF THE PREFERRED EMBODIMENTS

The present invention relates to a fiberoptic hose assembly that is utilized in conjunction with a conventional dental handpiece that utilizes fiberoptics. The handpiece is the device that is held in the hand of a dentist when he is performing certain dental operations in the oral cavity of a patient. These operations typically include drilling and filling cavities as well as cleaning teeth. The handpiece is an air-driven, turbine-powered device to which is attached the appropriate tool to allow the dentist to perform his operations.

The handpiece hose assembly connects the handpiece to the power supply which is located in a remote area of the dentist's office. Because the dentist works at a variety of angles to the oral cavity of the patient, it is preferable that the connection between the handpiece and the hose assembly be swivelable. The general working environment of the present invention is shown in U.S. Pat. No. 4,553,938 (Olsen), the disclosure of which is hereby incorporated by reference herein.

Figure 1:
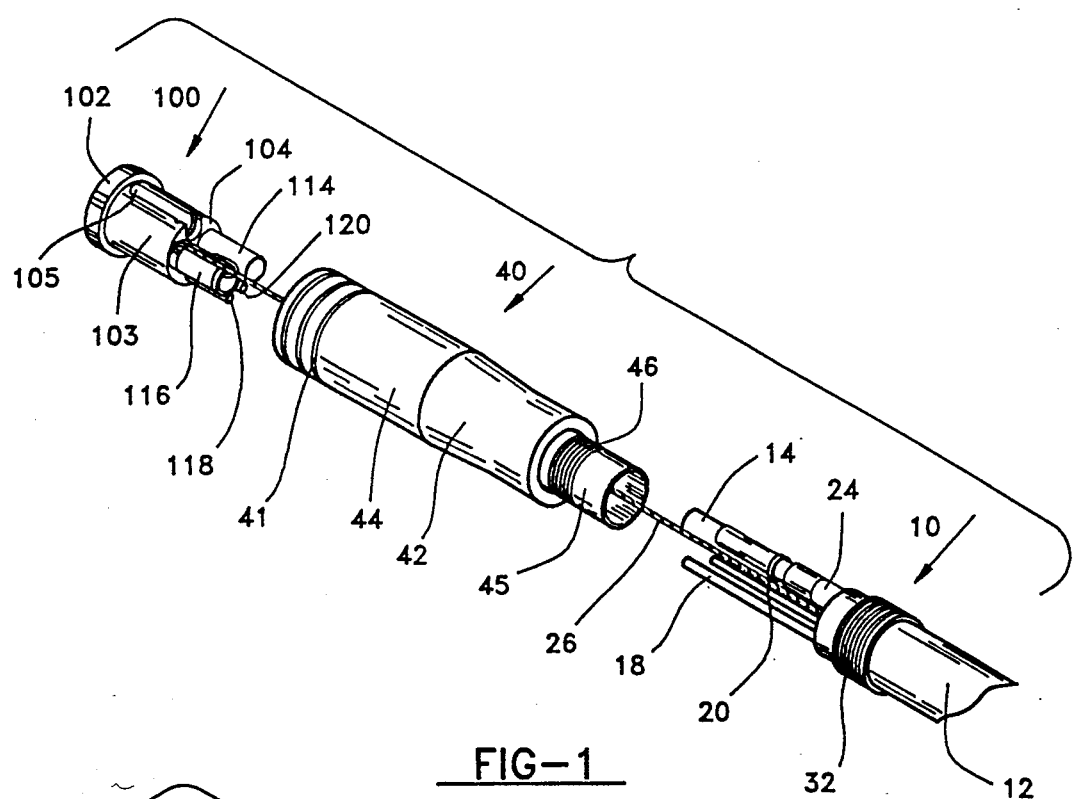
FIG. 1 is a perspective exploded view of the apparatus of the present invention.

As shown in FIG. 1 of the drawings, the fiberoptic hose assembly 10 of the present invention includes a smooth-walled rubber or plastic outer tubing 12. The outer tubing 12 is quite flexible and smooth on both its inner and outer surfaces. The smoothness of the outer surface makes the outer tubing quite aseptic and easily cleanable.

Conventional hose assembly tubings have been made from polyvinylchloride (PVC) materials and suffer the disadvantage of hardening and cracking over time. Oil is used as a lubricant in the high speed metal moving parts of the handpiece and the oil has a tendency to be carried rearwardly into the outer tubing when the air is exhausted from the interior of the handpiece. This oil reacts with the PVC and deteriorates the flexibility of the outer tubing.

In the preferred embodiment of the present invention, silicone treated polyurethane is used for the outer tubing 12. In the preferred embodiment, the particular silicone treated polyurethane is Model 11-2007-00-01, manufactured by Coaxco, Inc. P.O. Box 489, Tualatin, Ore. 97062. This silicone treated polyurethane is resistant to the oil and mitigates hardening and cracking of the outer tubing 12. The useful life of the outer tubing is greatly extended and it maintains the flexibility necessary to accommodate the twisting and rotating that the outer tubing undergoes during use.

Inside the outer tubing 12 are contained a plurality of components that are used to feed air, water and light to the handpiece. A first inner tubing 14 carries the drive air which operates the turbine in the handpiece to cause the tool connected to the handpiece to rotate at the high speeds required by modern dentistry. A second inner tubing 18 delivers "chip air" to the patient's oral cavity which is used to loosen debris that occurs during the drilling process. A third inner tubing 20 delivers coolant water to the patient's oral cavity. The remaining space in the outer tubing functions as a passageway for the return of exhaust air from the patient's oral cavity through the handpiece in a conventional manner.

A fiberoptic bundle 24 is also contained in the tubing along with a sensing cable 26. Each of these five components, along with the space for the return of the exhaust air, are easily provided inside the outer tubing 12. The outer tubing 12 being thin-walled and flexible makes it very easy to feed each of these components down the length of the outer tubing 12.

The ends of each of these five components are attached to an adapter 100 which, in turn, is connected to the particular handpiece and tool (not shown) that the dentist desires to use in the patient's oral cavity.

As shown in FIG. 1, disposed between the adapter 100 and the end of the outer tubing 12 is a swivel member 40. In this embodiment, the swivel member 40 is a component comprised of a front section 44, a center section 42 and a rear section 45. In the preferred embodiment, the front section 44 is made from stainless steel, the center section is made from durable plastic, such as Delrin ®, and the rear section is made from brass. The use of plastic for as many components as possible lowers the overall weight of the handpiece hose assembly 10, and particularly the swivel member 40 and mitigates the fatigue that the dentist suffers from extended use of the handpiece and handpiece hose assembly during a long day of work. It is preferred to utilize metal for the front section 44 since the interior of the front section 44 contains threads (not shown) that receive the threaded end of the handpiece.

In this embodiment of the present invention shown in FIG. 1, the swiveling occurs at the junction of the center section 42 and the rear section 45 as will be more fully explained in connection with FIG. 3. One end of the forward section 44 is provided with a series of serrated channels 41 to improve the gripability of the swivel member 40 when it is held by the dentist during use. The threaded interior (not shown) of the front section at approximately the location of the channels 41 permits connection of a handpiece by screwing the end of the handpiece into the front section 44 as is conventional in the art.

In this embodiment, the outer tubing 12 is joined to the rear section 45 of the swivel member 40 by means of a press fit coupled with the use of a compression spring. When these elements are assembled, the open end of the outer tubing 12 slides up over the open end of the rear section 45 until the outer tubing reaches the barb channels 46. The compression spring 32 is then slid up over the rear section until it reaches the location of the barb channels 46. The compression spring then forces the outer tubing into the barb channels 46 to hold the end of the outer tubing securely to the rear section 45 of the swivel member 40. This construction provides an airtight and watertight connection of the outer tubing to the swivel member. For aesthetic purposes, it is also desirable to provide a covering (not shown) over the compression spring 32. The covering can take any conventional form such as a sleeve of the same material from which the outer tubing is made or a wrapping of tape or any other similar covering.

In the fully assembled position, the adapter 100 is mounted inside the front section 44 of the swivel member 40 just rearwardly of the interior threads. The interior components of the outer tubing 12 are each individually connected to the adapter 100. The adapter 100 has a plurality of passageways therethrough. The passageways correspond to the air, water and light components contained within the outer tubing 12. The exit end 102 of the adapter 100 acts, in a manner well known in the art, as a "socket" into which is "plugged" the handpiece.

Figure 5:
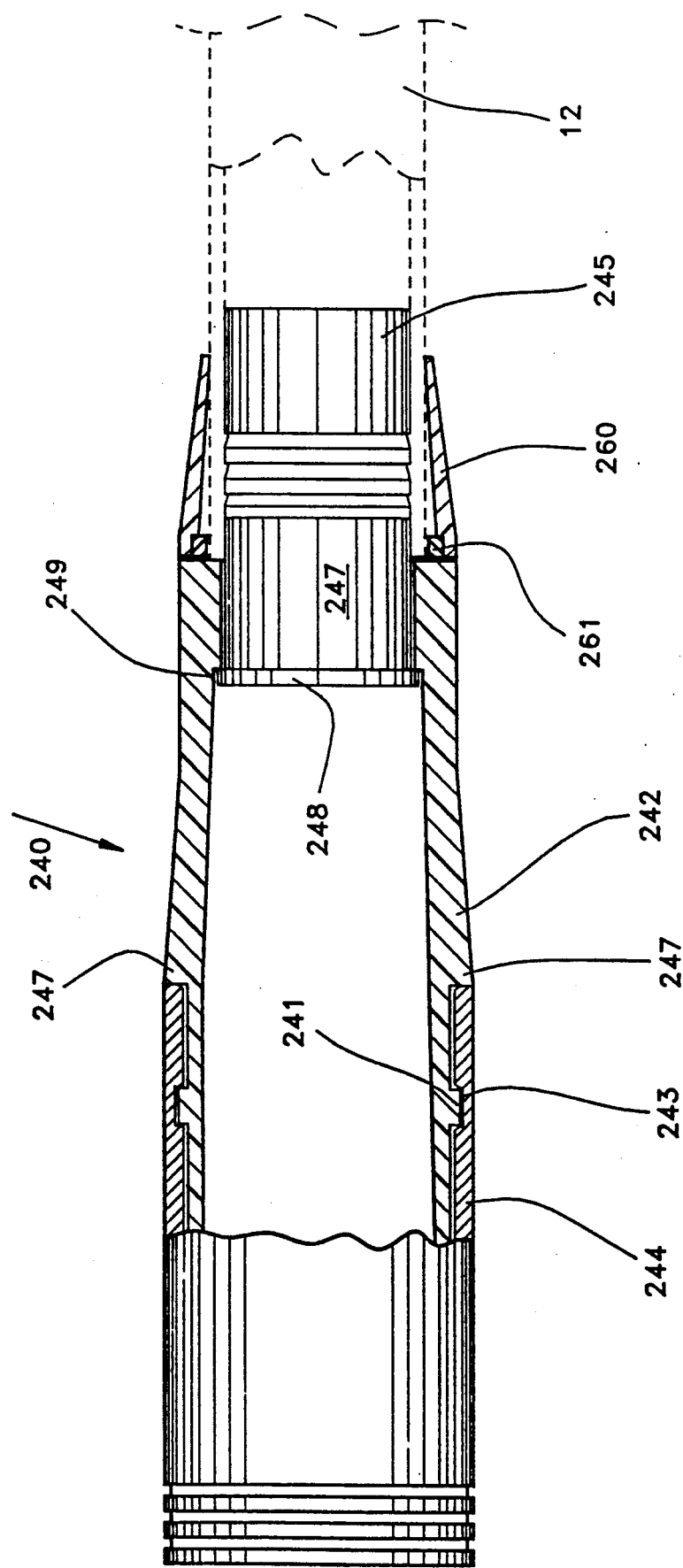
FIG. 5 is a side view partially in section of another alternate embodiment of the swivel member of the present invention.

The rearward end 104 of the adapter 100, as shown in FIGS. 1 and 5, is provided with a plurality of stems that act as the joining means for the air, water and light components contained in the outer tubing 12. In use, drive air stem 114 is the connection for the drive air tubing 14; exhaust air stem 116 is the opening for the exhaust air to be returned to the outer tubing; "chip" air stem 118 is the connection for the "chip" air tubing 18 and coolant water stem 120 is the connection for the coolant water tubing 20. Each stem is formed in the shape of a barb as disclosed and shown in the Olsen patent, above.

Each stem is hollow and is aligned with corresponding passageways in the body 103 of the adapter 100 so that the air, fluid and fiberoptic components can be continued into the handpiece. The body 103 of the adapter 100 is also provided with a channel 105 to receive the end of the fiberoptic bundle 24 in a manner which will be more fully explained in connection with FIG. 6.

Figure 6:
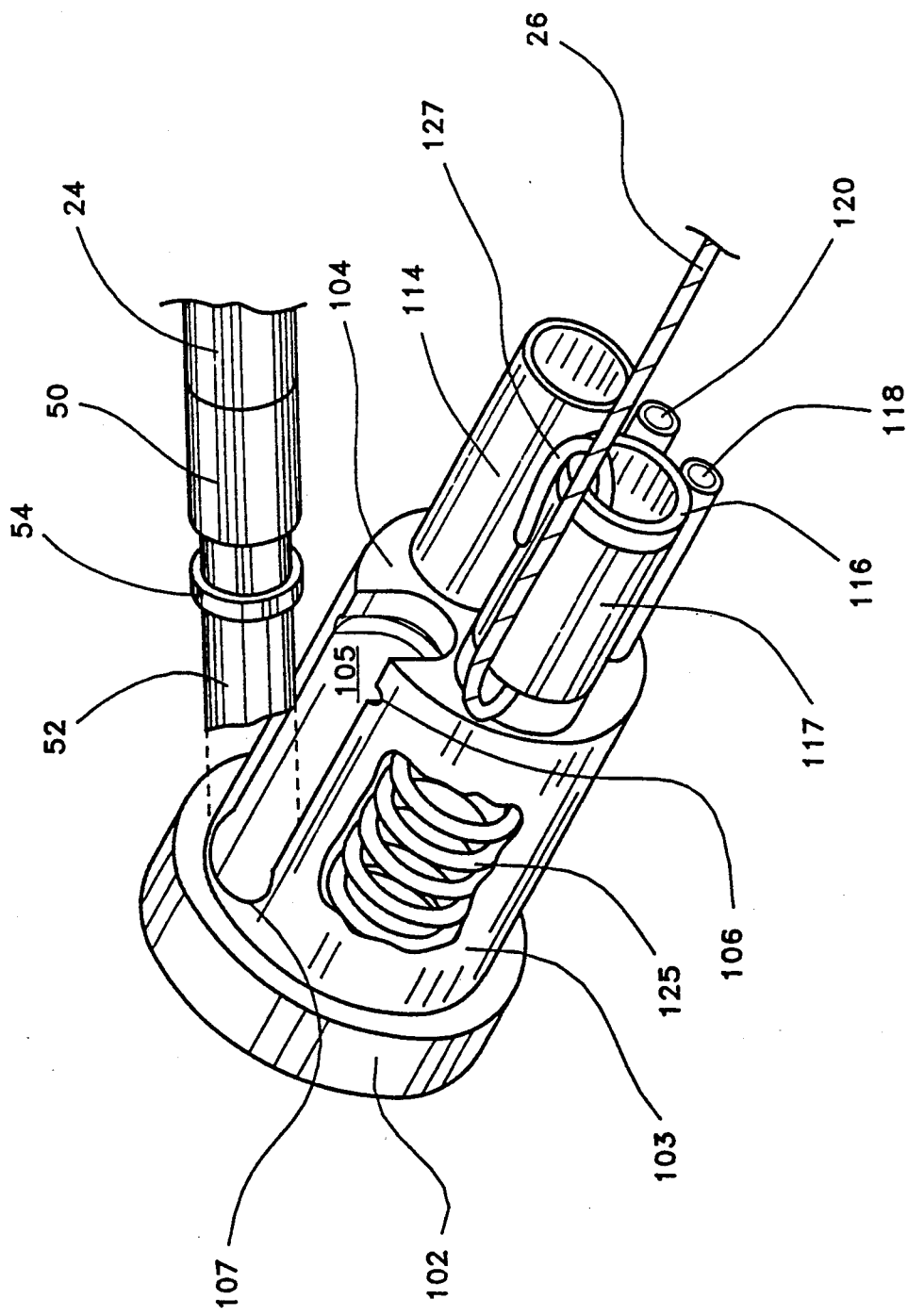
FIG. 6 shows a perspective view in detail of the adapter of the apparatus of the present invention.
Figure 7:
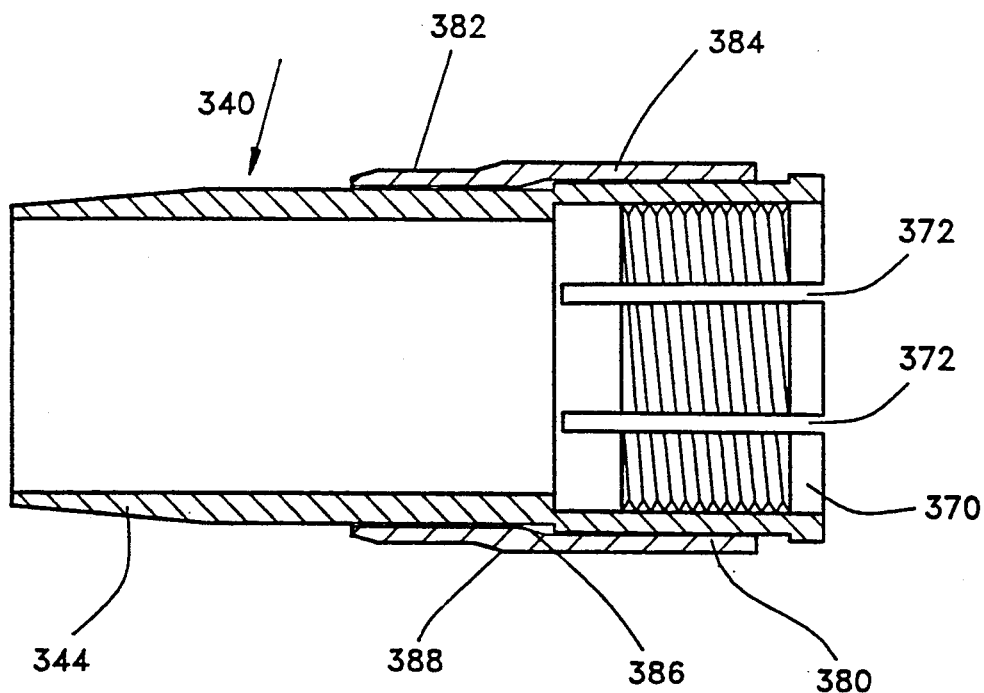
FIG. 7 is a side view of the quick disconnect construction of the present invention in the unlocked position.

The sensing cable 26 terminates at the adapter 100 in a manner shown more clearly in FIG. 6. The sensing cable 26 is passed through the swivel member 40 and then is secured to the exhaust air stem 116 in any conventional manner. In the preferred embodiment, to more securely hold the sensing cable 26 to the stem 116, a plastic wrapping tube 117 can be slid over the stem 116 and this holds the end of the sensing cable 26 to the stem 116. Since stems on adapters used in this type of dental equipment are typically barbed (as shown in the Olsen patent), the plastic wrapping tube 117 securely holds the end of the sensing cable 26 to the stem 116.

In a typical "touch-activated" assembly, when the dentist picks up the handpiece and hose assembly to begin work and touches the swivel connection, the fiberoptic bundle is activated. The necessary conductive path between the fiberoptic bundle and the handpiece is completed by utilizing a metal adapter. In a typical assembly, the adapter is made from a conductive material such as metal, so as soon as the dentist picks up the hose assembly, the conductive path is completed and the light source is activated illuminating the fiberoptic bundle. This is so even if there is no handpiece connected to the handpiece hose assembly.

In the preferred embodiment of the present invention, it is desirable to utilize a plastic adapter body 103 to again save weight and to insulate the swivel member 40 from the sensing cable 26. In order to complete the conductive path, a metal spring 125, preferably made of stainless steel, is provided in the interior of the adapter body 103 in alignment with the stem 116. The rear end of the spring 125 is provided with a hook 127 that connects to the stem 116 as shown in FIG. 6 to hold the spring in place.

When the handpiece is connected to the adapter 100, the end of the handpiece contacts the spring 125 and the conductive path is completed from the spring 125, through the hook 127 and stem 116 and finally the sensing cable 26. Thus when the dentist picks up the handpiece, the conductive path is completed and the light source is activated illuminating the fiberoptic bundle. If no handpiece is connected to the swivel member 40, the conductive path is not complete and no amount of handling of the swivel member 40 by the dentist will activate the light source.

The fiberoptic hose assembly of the present invention is "field-serviceable." This means that repairs to the fiberoptic hose assembly can be made in the dentist's office without the necessity of returning the entire assembly to the repair shop. In use, leaks or blockages will typically occur at or close to the location where the tubings connect to the adapter 100. By disassembling the adapter 100 from the swivel member 40, access can be had to the inner tubings to effect repairs.

Breaks also may occur in the fiberoptic bundle 26. In the preferred embodiment of the present invention, the outer sheathing of the fiberoptic bundle 24 is made from a translucent material so that if a break occurs in the fiberoptic bundle, the light emanating from the fiberoptic bundle at the point of the break will be visible through the outer sheathing. In the preferred embodiment, this outer sheathing is made from silicone-treated polyurethane similar to that used to make the outer tubing 12. In the preferred embodiment, the particular silicone treated polyurethane for the outer sheathing of the fiberoptic bundle is Model 11-2012-00-01, manufactured by Coaxco, Inc. P.O. Box 489, Tualatin, Ore. 97062. It is desirable to have the fiberoptic bundle 24 be oil resistant for the same reasons that the outer tubing 12 is desired to be oil resistant.

In order to repair these leaks, blockages or breaks, the repair person must have access to the adapter 100 and to the tubings connected to the adapter 100. In the preferred embodiment of the present invention, access is achieved by separating the adapter 100 from the forward section 44 of the swivel member 40. The adapter 100 can be slid forward out of the forward section 44 by grasping the adapter 100 with any suitable tool, such as a pair of needle nose pliers.

Because there is slack in the inner tubings contained within the outer tubing 12 and because the inner tubings are not attached to the outer tubing 12, both the adapter 100 and the inner tubings connected thereto can be moved slightly forward and apart from the forward section 44 of the swivel member 40 to allow the repair person to inspect the junctions of each tubing with its associated stem to determine if a leak or blockage is present. For example, if a leak or blockage is present in the coolant water tubing 20, it is simple matter for the repairman to clean out the blockage or repair the leak and then reconnect the coolant water tubing 20 to the stem 120. There is enough slack in the length of the water tubing 20 contained in the outer tubing 12 to permit a portion of the water tubing 20 to be removed and the remainder of the water tubing to be reconnected to the stem 120. Repairs to each of the other components can be effected in a similar manner.

In the preferred embodiment of the present invention, the inner tubings and the fiberoptic bundle are completely separable from the supply base (not shown) at the end of the hose assembly remote from the adapter. Therefore, if it is necessary to completely replace any of the inner tubings or the fiberoptic bundle, such replacement can take place in the dentist's office.

Figure 2:
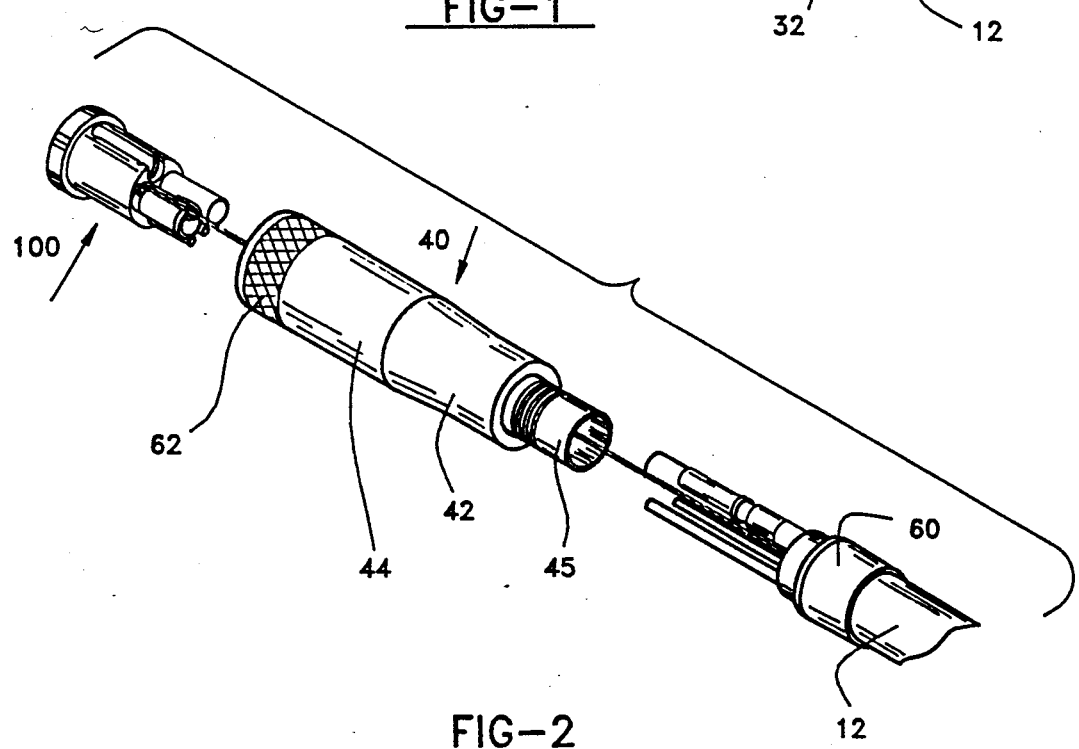
FIG. 2 is a perspective exploded view of an alternate embodiment of the apparatus of the present invention.

In order to provide for improved gripability of the swivel member by the dentist, the forward end of the front member 44 can be provided with a knurled surface 62 as shown in FIG. 2.

Figure 3:
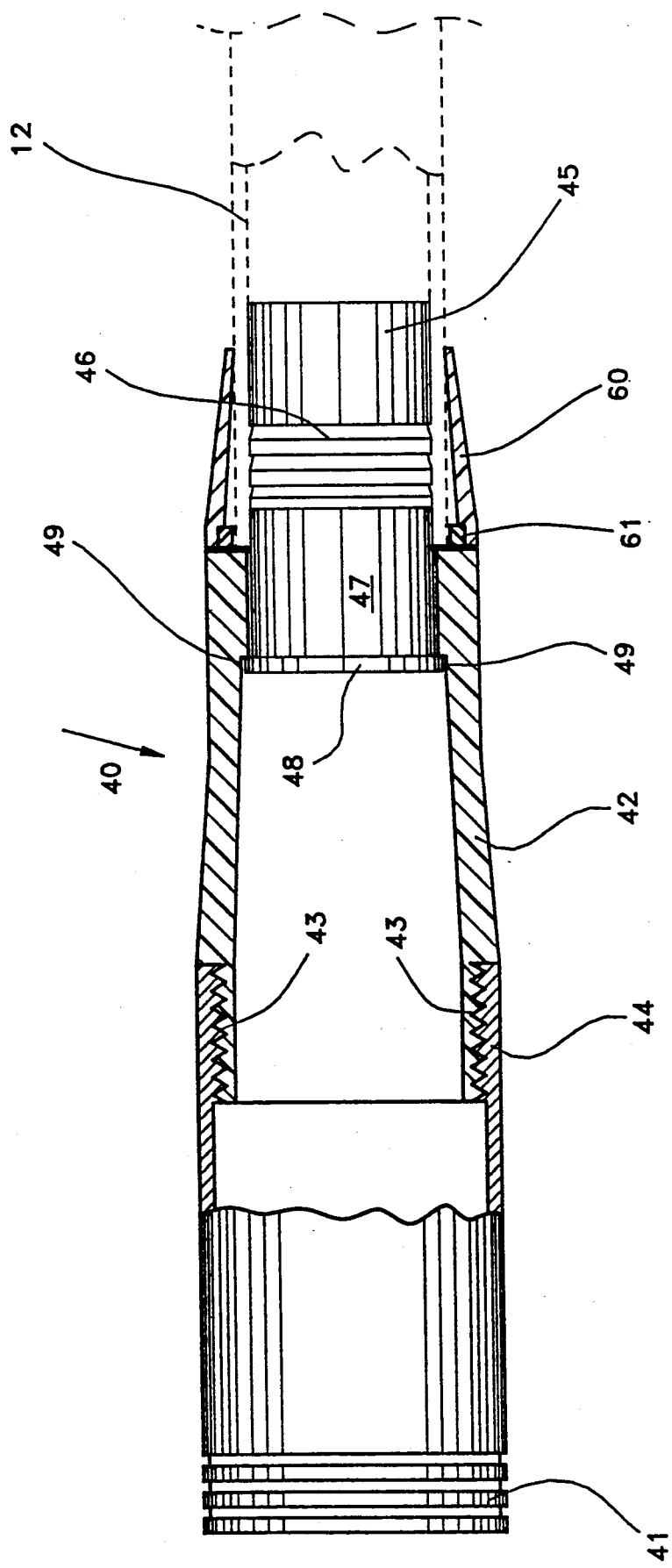
FIG. 3 is a side view partially in section of the swivel member of the present invention.

Also as shown in FIGS. 2 and 3, in lieu of the compression spring 32 shown in FIG. 1 to secure the outer tubing 12 to the rear section 45 of the swivel member 40, a compression cone 60 may be used. The compression cone 60 is a cylindrical frusto-conical member that will be slid up and over the connection of the outer tubing 12 onto the end of the rear section 45. The interior taper of the compression cone 60 is chosen to squeeze the outer tubing 12 against the rear section 45 as the compression cone 60 slides up and over the outer tubing 12. This is shown in clearer detail in FIG. 3. The compression cone 60 has a stepped inner recess that receives a Teflon ® bearing 61 to assist in holding the outer tubing 12 onto the rear section 45.

FIG. 3 also shows the detail of the swivel member 40 of a preferred embodiment of the present invention. The front section 44 is threadably attached at 43 to the center section 42, although other suitable connections can be utilized such as merely press fitting these two sections together. In this embodiment, the swiveling action occurs at the junction of the center section 42 and the rear section 45. The rear section 45 has an interior end 47 which is provided with a circumferential shoulder 48 that rides in a circumferential ledge 49 on the interior wall of the center section 42. As described above, the outer tubing 12 is securely fastened to the rear section 45 and the contact point of the shoulder 48 of the rear section on the ledge 49 of the center section 42 allows a swiveling action to occur between the outer tubing 12 and the center section 42.

It should be noted that the center section 42 has a slight taper. The center section is slightly larger in interior cross section at the end where it is connected to the front section 44 by threads 43 and becomes smaller in interior cross section toward the end where it is connected to the rear section 45. This taper permits the assembly of the rear section 45 into swivelable engagement with the center section 42 by feeding the rea section 45 down the interior of the center section 42 until the shoulder 48 on the rear section 45 comes into contact with the ledge 49 on the center section 42.

Figure 4:
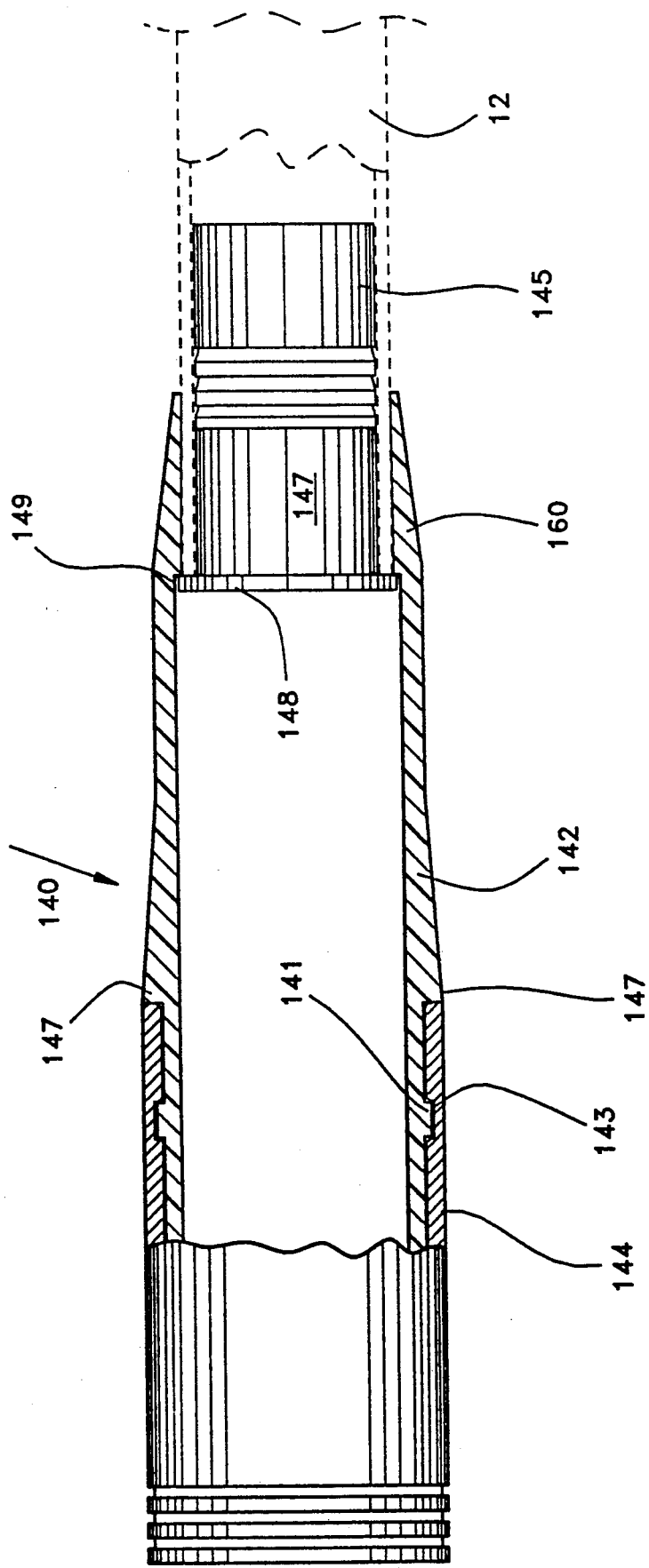
FIG. 4 is a side view partially in section of an alternate embodiment of the swivel member of the present invention.

Another preferred embodiment of the swivel member 140 is shown in FIG. 4. In this version, the swivel member rotates at the junction of the front section 144 and the center section 142. As described above, the outer tubing 12 is securely fastened to the rear section 145, however, in this embodiment the center section 142 has the compression ring 160 formed integrally therewith. While the rear section 145 still acts as a central support member for the interior of the outer tubing 12, the compression ring 160 securely holds the outer tubing 12 to the rear section 145 and the frictional forces will inhibit swiveling of the rear section 145 relative to the center section 142.

The swiveling is effected by the connection of the front section 144 to the center section 142. The front section 144 is provided with a circumferential slot 143 and the center section 142 is provided with a circumferential shoulder 141. In assembly, the forward end of the center section is slid up and into the rearward end of the front section 144 until the shoulder 141 on the center section pops into the slot 143 on the front section 144. A shoulder 147 on the center section 142 prevents the center section 142 from going too far into the front section 144. Once the center section 142 is popped into the forward section 144, swiveling can easily occur between these two sections as the shoulder 141 rides freely in the slot 143.

A double swivel arrangement of the present invention is shown in FIG. 5. In effect, this is a combination of the swivel shown in FIG. 3 and the swivel shown in FIG. 4. In this embodiment, the first swiveling action occurs at the junction of the center section 242 and the rear section 245. The rear section 245 has an interior end 247 which is provided with a circumferential shoulder 248 that rides in a circumferential ledge 249 on the interior wall of the center section 242. As described above, the outer tubing 12 is securely fastened to the rear section 245 and the contact point of the shoulder 248 of the rear section on the ledge 249 of the center section 242 allows a swiveling action to occur between the outer tubing 12 and the center section 242.

The second swiveling action occurs at the junction of the front section 244 and the center section 242 The swiveling is effected by the connection of the front section 244 to the center section 242 The front section 244 is provided with a circumferential slot 243 and the center section 242 is provided with a circumferential shoulder 241. In assembly, the forward end of the center section is slid up and into the rearward end of the front section 244 until the shoulder 24 on the center section pops into the slot 243 on the front section 244. A shoulder 247 on the center section 242 prevents the center section 242 from going too far into the front section 244. Once the center section 242 is popped into the forward section 244, swiveling can easily occur between these two sections as the shoulder 241 rides freely in the slot 243. This double swivel arrangement provides very high rotatability to the swivel member and makes the handpiece quite easy to use.

As shown in FIG. 6, one particular advantage of this assembly arrangement of the present invention is that the fiberoptic bundle 24 is easily accessible to the repair person when the adapter 100 is slid out of the forward section 44 of the swivel member 40. The fiberoptic bundle 24 is provided with a connection member 52 which is secured to the end of the fiberoptic bundle 24 by means of a ring clamp 50. The connection member 52 has a mounting ring 54 for attaching the fiberoptic bundle 24 to the adapter 100.

The attachment of the connection member 52 of the fiberoptic bundle 24 to the adapter is shown in FIG. 6. The forward end of the connection member 52 is slid at an angle into the channel 105 of the adapter 100. The end 107 of the channel 105 is slightly enlarged to permit the connection member to be slid therein. The mounting ring 54 is aligned with a slot 106 in the channel member 105 and the connection member 52 is popped into the channel 105. The engagement of the mounting ring 54 within the slot 106 prevents forward or rearward movement of the connection member 52 (and thus the fiberoptic bundle 24) when it is connected to the adapter 100. When servicing of the assembly is desired, the connection member 52 can be popped out of the channel 105.

After removal of the connection member 52 from the adapter 100, the fiberoptic bundle 24 can be utilized as a light source by the repair person to help look at and inspect the other tubings to determine the source of the leak or blockage. Another advantage of this construction is that the fiberoptic bundle 24 can be released from the adapter 100 and moved slightly out of the way while the repairs are made either to the fiberoptic bundle 24 or to the inner tubings or the adapter 100. This minimizes the possibility of causing damage to the fiberoptic bundle 24 during repairs. This is particularly important since the fiberoptic bundle 24 is usually quite fragile.

Once the necessary repairs have been completed, it is a simple matter for the repair person to reconnect all of the tubings to their respective stems in the adapter 100. The fiberoptic bundle 24 is then reinserted into the channel 105 in the adapter 100 and the adapter is slid back into the swivel member 40.

FIGS. 7 through 10 show a quick disconnect construction for attaching the swivel member 40 to a handpiece 400. The front section 344 of a swivel member is provided with a interiorly threaded female section 370. The threaded female section 370 is a hollow tubular piece around whose circumference there is provided a plurality of spaced expansion slots 372. Because a plurality of expansion slots 372 have been provided, in the unlocked position shown in FIG. 7, the diameter of the threaded female section 370 is slightly larger than the diameter of the corresponding threaded male section 402 on the end of the handpiece 400 which is to be connected to the swivel member.

A locking collar 380 is mounted around the front section 344 and the threaded female member 370. The locking collar comprises a back ring 382 just slightly larger in diameter than the outer diameter of the front section 344 so that the locking collar 380 can slide along the surface of the front section 344. The locking collar also has a front ring 384 just slightly larger in diameter than the outer diameter of the threaded female section 370 so that the locking collar 380 can slide along the surface of the front section 344. The outer surface of the locking collar 380 has an outer transition point 386 where the back and front outer diameters of the locking collar 380 meet. The inner surface of the locking collar 380 has an inner transition point 388 where the back and front inner diameters of the locking collar 380 meet.

Figure 8:
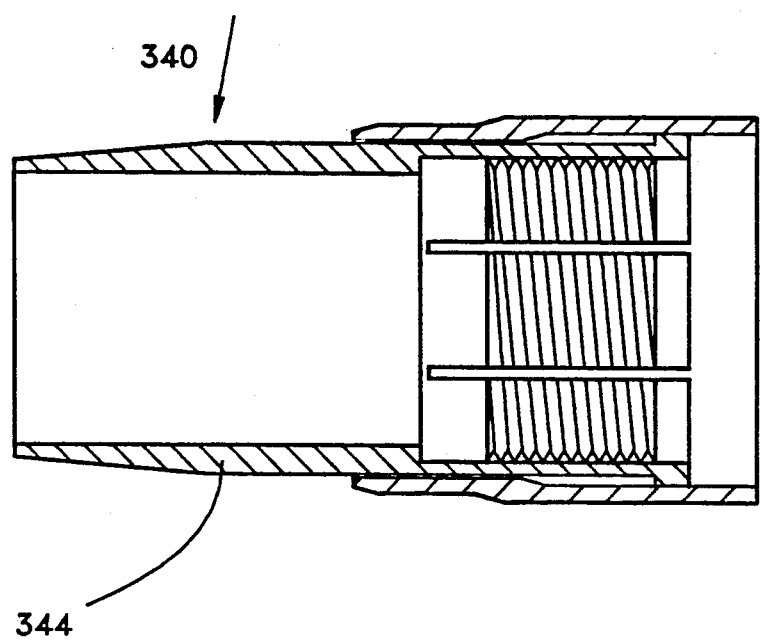
FIG. 8 is a side view of the quick disconnect construction of the present invention in the locked position.
Figure 9:
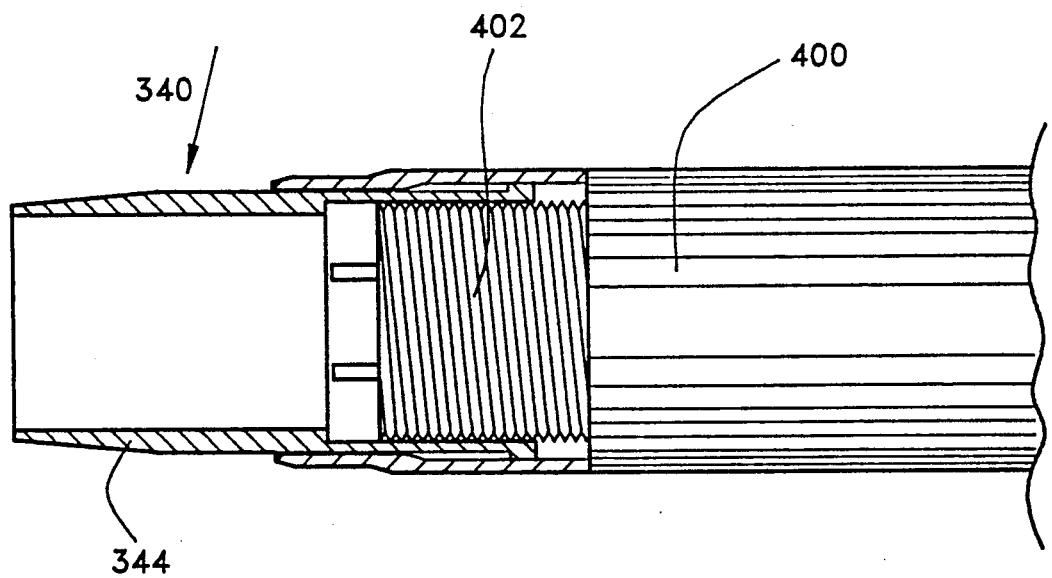
FIG. 9 is a side view of the quick disconnect construction of the present invention in the locked position with the threaded end of a handpiece inserted therein.

FIGS. 8 and 9 illustrate the operation of the locking collar 380 and shows the locking collar 380 in its locked position. To effect a quick connection of the handpiece 400 to the swivel member 340, the user inserts the threaded male member 402 of the handpiece into the expanded female threaded section 370. Because the threaded female section 380 has been provided with expansion slots 372, the threaded male member 402 easily slides into place without having to be threaded. This eliminates the time necessary in a conventional assembly to screw the full length of the male member into the female member.

Once the male threaded member 402 is slid into the threaded female member 370, the locking collar 380 is grasped in a hand of the user and slid forward. The outer transition point 386 provides a convenient ridge so that the users hand can grasp the locking collar 380 and move it forward. As the locking collar 380 moves forward, the inner transition point 388 wedges against the threaded female section 370 and, in effect, squeezes the threaded female section 370 into a smaller diameter. This change in diameter is accommodated by the expansion slots 372 so no deformation of the threads takes place. The threads on the threaded female section 370 close in around the threads on the threaded male section 402 and secure the handpiece 400 to the swivel member 340. If necessary, a slight turn of the handpiece 400 or the swivel member 340 can be made to seat the threads into a fully locked position.

A quick disconnect of the handpiece 400 from the swivel member 340 is easily effected. The user grasps the locking collar and simply slides it backwards. The threaded female member 370 expands slightly due to the expansion slots 372 and the threaded male member 402 on the handpiece 400 can easily be slid out of the swivel member 340.

Figure 10:
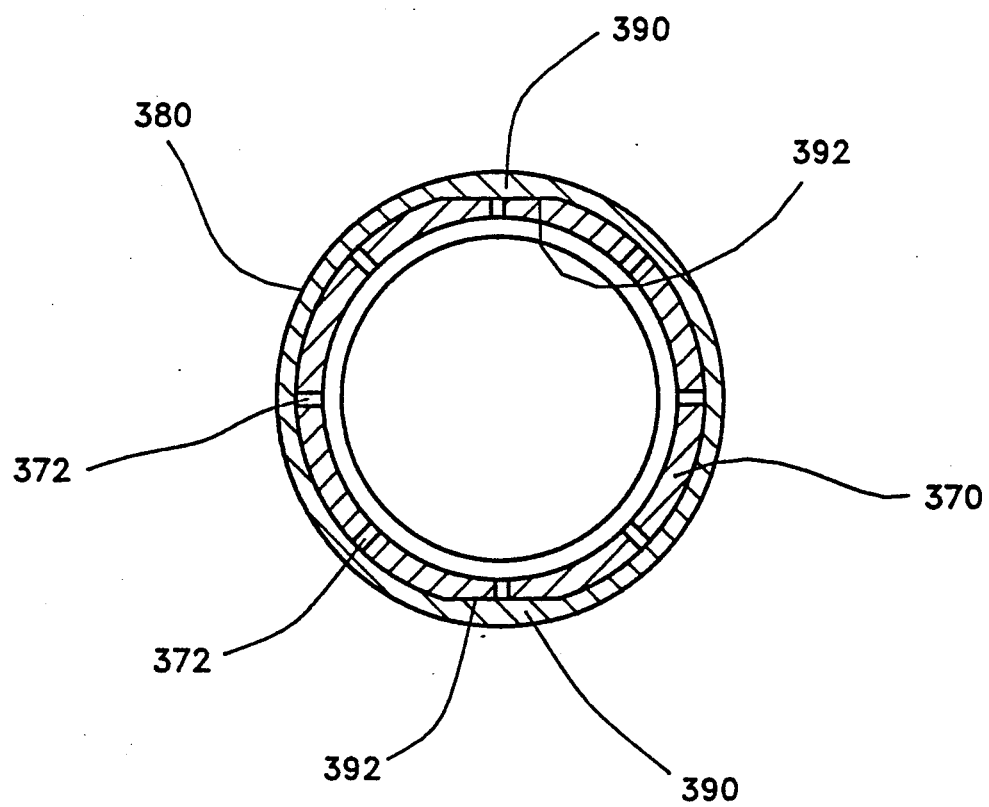
FIG. 10 is an end view of a preferred embodiment of the quick disconnect construction of the present invention.

FIG. 10 shows an alternative embodiment of the quick disconnect construction. At diametrically opposed locations around the circumference of the locking collar 380, flat edges 390 are provided. Similarly, at diametrically opposed locations around the circumference of the threaded female member 370, flat bevels 392 are provided. The flat edges 390 cooperate with the flat bevels 392 to align the locking collar 380 with the threaded female member 370 and to prevent the locking collar 380 from inadvertently rotating around the threaded female member 370.

The fiberoptic hose assembly of the present invention is also an aseptic design—that is, the design of the fiberoptic hose assembly is intended to inhibit and minimize the possibility of bacteria collecting on the surfaces of the fiberoptic hose assembly. The outer tubing 12 is completely smooth-walled and does not have any creases, bends or surface irregularities that would provide locations at which bacteria could collect. The smooth-walled configuration of the outer tubing 12 makes cleaning quite easy.

The fiberoptic bundle 24 can be made from the conventional glass fiberoptic material that is currently in use. The fiberoptic bundle 24 is made up of a plurality of glass fibers having the property of transmitting light. Each glass fiber has a typical cross-section of approximately 0.001 inches. The resulting fiberoptic bundle has an overall diameter of generally between 0.073 and 0.093 inches.

As an alternative to the glass fiberoptic bundles currently in use, the fiberoptic bundle 24 is preferably made of an acrylic material that will transmit light. Suitable acrylics that can be used as the fiberoptic bundle are manufactured under the tradename LUMILEEN by Poly-optical Products, Inc, 1815 Carnegie Avenue, Santa Ana, Calif. 92705. A fiberoptic bundle made from these acrylics is much lighter in weight and much more flexible than the conventional glass fiberoptic bundles now in use. The fiberoptic bundles made from acrylic and used in the preferred embodiment of the present invention are made up of fibers that each have a diameter of approximately 0.010 inches and the overall fiberoptic bundle diameter is approximately 0.100 inches.

While the invention has been illustrated with respect to several specific embodiments thereof, these embodiments should be considered as illustrative rather than limiting. Various modifications and additions may be made and will be apparent to those skilled in the art. Accordingly, the invention should not be limited by the foregoing description, but rather should be defined only by the following claims.

What is claimed is:

1. A dental handpiece hose assembly comprising
   (a) an outer tubing,
   (b) a plurality of inner tubings carried within the outer tubing, said inner tubings providing conduits for drive air, chip air and coolant water as well as an air exhaust conduit,
   (c) a fiberoptic bundle carried within the outer tubing,
   (d) a sensing cable carried within the outer tubing,
   (e) an adapter for connecting an end of each inner tubing and the fiberoptic bundle to a dental handpiece, and
   (f) a generally hollow swivel member having a front section, a center section attached to the front section and a rear section swivelably attached to the center section, the rear section being attached to the outer tubing,
   (g) the adapter slidably mounted into the front section of the swivel member to permit the adapter to be accessible for repairs.

2. The dental handpiece hose assembly of claim 1 wherein a compression spring is mounted on the center section and compresses the outer tubing between the center section and the rear section.

3. The dental handpiece hose assembly of claim 1 wherein a compression cone is mounted on the center section and compresses the outer tubing between the center section and the rear section.

4. The dental handpiece hose assembly of claim 1 wherein the rear section includes a shoulder that engages a ledge on the center section to effect the swivelable attachment of the rear section and the center section.

5. The dental handpiece hose assembly of claim 1 wherein the front section includes at least one serrated channel to improve the gripability of the swivel member.

6. The dental handpiece hose assembly of claim 1 wherein the front section includes a knurled surface to improve the gripability of the swivel member.

7. The dental handpiece hose assembly of claim 1 wherein the adapter has at leastoen stem to which is connected the sensing cable.

8. A dental handpiece hose assembly comprising:
   (a) an outer tubing,
   (b) a plurality of inner tubings carried within the outer tubing, said inner tubings providing conduits for drive air, chip air and coolant water as well as an air exhaust conduit,
   (c) a fiberoptic bundle carried within the outer tubing,
   (d) a sensing cable carried within the outer tubing,
   (e) an adapter for connecting an end of each inner tubing and the fiberoptic bundle to a dental handpiece,
   (f) a swivel member having a front section for slidably receiving the adapter therein, a center section attached to the front section and a rear section swivelably attached to the center section, the rear section being attached to the outer tubing,
   (g) the adapter having at least one stem to which is connected the sensing cable and a conductive spring mounted in the adapter so that the sensing cable is in conductive communication with the adapter when a handpiece is attached thereto.

9. The dental handpiece hose assembly of claim 8 further including a hook attached to the end of the conductive spring for securing the conductive spring to the stem of the adapter to which is attached the sensing cable.

10. The dental handpiece hose assembly of claim 9 further including a plastic tube disposed around the stem to secure the sensing cable to the stem.

11. The dental handpiece hose assembly of claim 1 wherein the adapter includes a channel in which is mounted the fiberoptic bundle.

12. The dental handpiece hose assembly of claim 11 wherein the fiberoptic bundle includes a connection member that fits into the channel in the adapter to secure the fiberoptic bundle to the adapter.

13. The dental handpiece hose assembly of claim 12 wherein the connection member further includes a mounting ring that fits into a cooperating slot in the channel on the adapter to more securely hold the fiberoptic bundle to the adapter.

14. The dental handpiece hose assembly of claim 1 wherein the outer tubing is made from a silicone treated polyurethane material.

15. The dental handpiece hose assembly of claim 1 wherein the fiberoptic bundle has a translucent outer sheathing.

16. The dental handpiece hose assembly of claim 1 wherein the fiberoptic bundle has an outer sheathing made from a silicone treated polyurethane material.

17. A dental handpiece hose assembly comprising:
   (a) an outer tubing,
   (b) a plurality of inner tubings carried within the outer tubing, said inner tubings providing conduits for drive air, chip air and coolant water as well as an air exhaust conduit,
   (c) a fiberoptic bundle carried within the outer tubing,
   (d) a sensing cable carried within the outer tubing,
   (e) an adapter for connecting an end of each inner tubing and the fiberoptic bundle to a dental handpiece,
   (f) a swivel member having a front section for slidably receiving the adapter therein, a center section attached to the front section and a rear section swivelably attached to the center section, the rear section being attached to the outer tubing, and (g) the adapter including a channel in which is mounted the fiberoptic bundle, the fiberoptic bundle including a connection member that fits into the channel to secure the fiberoptic bundle to the adapter, the connection member further including a mounting ring that fits into a cooperating slot in the channel to more securely hold the fiberoptic bundle to the adapter and a ring clamp to attach the connection member to the fiberoptic bundle.

18. A dental handpiece hose assembly comprising:
(a) an outer tubing,
(b) a plurality of inner tubings carried within the outer tubing, said inner tubings providing conduits for drive air, chip air and coolant water as well as an air exhaust conduit,
(c) a fiberoptic bundle carried within the outer tubing,
(d) a sensing cable carried within the outer tubing,
(e) an adapter for connecting an end of each inner tubing and the fiberoptic bundle to a dental handpiece, and
(f) a generally hollow swivel member having a front section, a center section attached to the front section and a rear section swivelably attached to the front section, the rear section being attached to the outer tubing,
(g) the adapter slidably mounted into the front section of the swivel member to permit the adapter to be accessible for repairs.

19. The dental handpiece hose assembly of claim 18 wherein a compression spring is mounted on the center section and compresses the outer tubing between the center section and the rear section.

20. The dental handpiece hose assembly of claim 18 wherein a compression cone is mounted on the center section and compresses the outer tubing between the center section and the rear section.

21. The dental handpiece hose assembly of claim 18 wherein the center section includes a shoulder that engages a slot in the front section to effect the swivelable attachment of the center section and the front section.

22. The dental handpiece hose assembly of claim 18 wherein the front section includes at least one serrated channel to improve the gripability of the swivel member.

23. The dental handpiece hose assembly of claim 18 wherein the front section includes a knurled surface to improve the gripability of the swivel member.

24. The dental handpiece hose assembly of claim 18 wherein the adapter has at least one stem to which is connected the sensing cable.

25. The dental handpiece hose assembly of claim 18 wherein the adapter includes a channel in which is mounted the fiberoptic bundle.

26. The dental handpiece hose assembly of claim 25 wherein the fiberoptic bundle includes a connection member that fits into the channel in the adapter to secure the fiberoptic bundle to the adapter.

27. The dental handpiece hose assembly of claim 26 wherein the connection member further includes a mounting ring that fits into a cooperating slot in the channel on the adapter to more securely hold the fiberoptic bundle to the adapter.

28. The dental handpiece hose assembly of claim 18 wherein the outer tubing is made from a silicone treated polyurethane material.

29. The dental handpiece hose assembly of claim 18 wherein the fiberoptic bundle has a translucent outer sheathing.

30. The dental handpiece hose assembly of claim 18 wherein the fiberoptic bundle has an outer sheathing made from a silicone treated polyurethane material.

31. A handpiece hose assembly comprising:
(a) an outer tubing,
(b) a plurality of inner tubings carried within the outer tubing, said inner tubings providing conduits for drive air, chip air and coolant water as well as an air exhaust conduit,
(c) a fiberoptic bundle carried within the outer tubing,
(d) a sensing cable carried within the outer tubing,
(e) an adapter for connecting an end of each inner tubing and the fiberoptic bundle to a dental handpiece,
(f) a swivel member having a front section for slidably receiving the adapter therein, a center section attached to the front section and a rear section swivelably attached to the center section, the rear section being attached to the outer tubing, and
(g) the adapter having at least one stem to which is connected the sensing cable and a conductive spring mounted in the adapter so that the sensing cable is in conductive communication with the adapter when a handpiece is attached thereto.

32. The dental handpiece hose assembly of claim 35 further including a hook attached to the end of the conductive spring for securing the conductive spring to the stem of the adapter to which is attached the sensing cable.

33. The dental handpiece hose assembly of claim 35 further including a plastic tube disposed around the air exhaust stem to secure the sensing cable to the air exhaust stem.

34. A dental handpiece hose assembly comprising:
(a) an outer tubing,
(b) a plurality of inner tubings carried within the outer tubing, said inner tubings providing conduits for drive air, chip air and coolant water as well as an air exhaust conduit,
(c) a fiberoptic bundle carried within the outer tubing,
(d) a sensing cable carried within the outer tubing,
(e) an adapter for connecting an end of each inner tubing and the fiberoptic bundle to a dental handpiece,
(f) a swivel member having a front section for slidably receiving the adapter therein, a center section attached to the front section and a rear section swivelably attached to the center section, the rear section being attached to the outer tubing, and
(g) the adapter including a channel in which is mounted the fiberoptic bundle, the fiberoptic bundle including a connection member that fits into the channel to secure the fiberoptic bundle to the adapter, the connection member further including a mounting ring that fits into a cooperating slot in the channel to more securely hold the fiberoptic bundle to the adapter and a ring clamp to attach the connection member to the fiberoptic bundle.

35. A dental handpiece hose assembly comprising:
(a) an outer tubing,
(b) a plurality of inner tubings carried within the outer tubing, said inner tubings providing conduits for drive air, chip air and coolant water as well as an air exhaust conduit, (c) a fiberoptic bundle carried within the outer tubing, (d) a sensing cable carried within the outer tubing, (e) an adapter for connecting an end of each inner tubing and the fiberoptic bundle to a dental handpiece, and (f) a generally hollow swivel member having a front section, a center section attached to the front section and a rear section swivelably attached to the center section, the rear section being attached to the outer tubing, (g) the adapter slidably mounted into the front section of the swivel member to permit the adapter to be accessible for repairs.

36. The dental handpiece hose assembly of claim 35 wherein a compression spring is mounted on the center section and compresses the outer tubing between the center section and the rear section.

37. The dental handpiece hose assembly of claim 35 wherein a compression cone is mounted on the center section and compresses the outer tubing between the center section and the rear section.

38. The dental handpiece hose assembly of claim 35 wherein the rear section includes a shoulder that engages a ledge on the center section to effect the swivelable attachment of the rear section and the center section.

39. The dental handpiece hose assembly of claim 35 wherein the center section includes a shoulder that engages a slot in the front section to effect the swivelable attachment of the center section and the front section.

40. The dental handpiece hose assembly of claim 35 wherein the rear section includes a shoulder that engages a ledge on the center section to effect the swivelable attachment of the rear section and the center section and the center section includes a shoulder that engages a slot in the front section to effect the swivelable attachment of the center section and the front section.

41. The dental handpiece hose assembly of claim 35 wherein the front section includes at least one serrated channel to improve the gripability of the swivel member.

42. The dental handpiece hose assembly of claim 35 wherein the front section includes a knurled surface to improve the gripability of the swivel member.

43. The dental handpiece hose assembly of claim 35 wherein the adapter has at least one stem to which is connected the sensing cable.

44. The dental handpiece hose assembly of claim 35 wherein the adapter includes a channel in which is mounted the fiberoptic bundle.

45. The dental handpiece hose assembly of claim 44 wherein the fiberoptic bundle includes a connection member that fits into the channel in the adapter to secure the fiberoptic bundle to the adapter.

46. The dental handpiece hose assembly of claim 45 wherein the connection member further includes a mounting ring that fits into a cooperating slot in the channel on the adapter to more securely hold the fiberoptic bundle to the adapter.

47. The dental handpiece hose assembly of claim 35 wherein the outer tubing is made from a silicone treated polyurethane material.

48. The dental handpiece hose assembly of claim 35 wherein the fiberoptic bundle has a translucent outer sheathing.

49. The dental handpiece hose assembly of claim 35 wherein the fiberoptic bundle has an outer sheathing made from a silicone treated polyurethane material.

50. A dental handpiece hose assembly comprising:
(a) an outer tubing,
(b) a plurality of inner tubings carried within the outer tubing, said inner tubings providing conduits for drive air, chip air and coolant water as well as an air exhaust conduit,
(c) a fiberoptic bundle carried within the outer tubing,
(d) a sensing cable carried within the outer tubing,
(e) an adapter for connecting an end of each inner tubing and the fiberoptic bundle to a dental handpiece,
(f) a swivel member having a front section for slidably receiving the adapter therein, a center section attached to the front section and a rear section swivelably attached to the center section, the rear section being attached to the outer tubing,
(g) the adapter having at least one stem to which is connected the sensing cable and a conductive spring mounted in the adapter so that the sensing cable is in conductive communication with the adapter when a handpiece is attached thereto.

51. The dental handpiece hose assembly of claim 50 further including a hook attached to the end of the conductive spring for securing the conductive spring to the stem of the adapter to which is attached the sensing cable.

52. The dental handpiece hose assembly of claim 51 further including a plastic tube disposed around the air exhaust stem to secure the sensing cable to the air exhaust stem.

53. A dental handpiece hose assembly comprising:
(a) an outer tubing,
(b) a plurality of inner tubings carried within the outer tubing, said inner tubings providing conduits for drive air, chip air and coolant water as well as an air exhaust conduit,
(c) a fiberoptic bundle carried within the outer tubing,
(d) a sensing cable carried within the outer tubing,
(e) an adapter for connecting an end of each inner tubing and the fiberoptic bundle to a dental handpiece,
(f) a swivel member having a front section for slidably receiving the adapter therein, a center section attached to the front section and a rear section swivelably attached to the center section, the rear section being attached to the outer tubing,
(g) the adapter including a channel in which is mounted the fiberoptic bundle, the fiberoptic bundle including a connection member that fits into the channel to secure the fiberoptic bundle to the adapter, the connection member further including a mounting ring that fits into a cooperating slot in the channel to more securely hold the fiberoptic bundle to the adapter and a ring clamp to attach the connection member to the fiberoptic bundle.

54. A dental handpiece hose assembly comprising:
(a) an outer tubing,
(b) a plurality of inner tubings carried within the outer tubing, said inner tubings providing conduits for drive air, chip air and coolant water as well as an air exhaust conduit, (c) a fiberoptic bundle carried within the outer tubing, (d) a sensing cable carried within the outer tubing, (e) an adapter for connecting an end of each inner tubing and the fiberoptic bundle to a dental handpiece, (f) a swivel member having a front section for slidably receiving the adapter therein, a rear section swivelably attached to the front section, the rear section being attached to the outer tubing, and (g) a quick disconnect construction mounted on the front section of the swivel member so that a handpiece can easily be connected or disconnected to the swivel member, the quick disconnect construction comprising a generally cylindrical hollow internally threaded female member having at least one expansion slot and a generally cylindrical hollow locking collar axially slidably mounted on the female threaded member so that the female threaded member can be compressed around a male threaded member by sliding movement of the locking collar, further including at least one flat edge on the internal surface of the locking collar and at least one cooperating flat bevel on the external surface of the female threaded member so that the locking collar can be aligned with the female threaded member.

55. The dental handpiece hose assembly of claim 54 wherein the quick disconnect construction further comprises an inner transition point on the locking collar that compresses the female threaded member as the locking collar is slid to a locking position.

56. The dental handpiece hose assembly of claim 55 wherein the quick disconnect construction further comprises an outer transition point on the locking collar that permits a user to grasp the locking collar during use.

57. The dental handpiece hose assembly of claim 54 wherein the locking collar has two flat edges diametrically disposed and the female threaded member has two flat bevels diametrically disposed. swivelably attached to the center section, the rear section being attached to the outer tubing,

* * * * *